US012714399B2

(12) United States Patent
Schou et al.

(10) Patent No.: US 12,714,399 B2
(45) Date of Patent: Aug. 25, 2026

(54) SYSTEM AND METHOD FOR DISPLAYING A VISUAL INDICATOR THAT INDICATES A MOVEMENT DIRECTION OF AN ULTRASOUND PROBE RELATIVE TO AN ULTRASOUND IMAGE

(71) Applicant: GE Precision Healthcare LLC, Waukesha, WI (US)

(72) Inventors: Mikkel Schou, Roskilde (DK); Svetoslav Nikolov, Søborg (DK)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/645,845

(22) Filed: Apr. 25, 2024

(65) Prior Publication Data

US 2025/0331821 A1 Oct. 30, 2025

(51) Int. Cl.
*A61B 8/00* (2006.01)
*A61B 90/90* (2016.01)

(52) U.S. Cl.
CPC ............ *A61B 8/463* (2013.01); *A61B 8/4254* (2013.01); *A61B 8/54* (2013.01); *A61B 90/90* (2016.02)

(58) Field of Classification Search
CPC .......... A61B 8/463; A61B 8/4254; A61B 8/54
See application file for complete search history.

(56) References Cited

U.S. PATENT DOCUMENTS 10,531,858 B2 1/2020 Lachaine et al.
10,646,199 B2 5/2020 Pelissier et al.
2010/0010348 A1* 1/2010 Halmann ............ A61B 8/0841 600/443
2011/0282207 A1* 11/2011 Hashimoto ............ A61B 8/466 600/443
2012/0330151 A1* 12/2012 Weinstein ............ A61B 8/4254 600/425
2019/0307425 A1* 10/2019 Jensen ................ A61B 8/4263
2022/0148199 A1 5/2022 Bauer et al.
2022/0338836 A1 10/2022 Doron et al.

FOREIGN PATENT DOCUMENTS

WO WO-2015075612 A1 * 5/2015 ............ A61B 8/463

* cited by examiner

*Primary Examiner* — Andrew W Begeman
(74) *Attorney, Agent, or Firm* — SPQ IP LLC

(57) ABSTRACT

Various systems and methods are provided for displaying a visual indicator that indicates a movement direction of an ultrasound probe relative to an ultrasound image. Ultrasound data corresponding to a scan plane of the ultrasound probe may be received. The ultrasound image corresponding to the scan plane of the ultrasound probe may be generated using the ultrasound data. The ultrasound image corresponding to the scan plane of the ultrasound probe may be displayed. A representation of the ultrasound probe that is oriented relative to the scan plane corresponding to the ultrasound image may be displayed. A movement direction of the ultrasound probe relative to the ultrasound image may be determined. The visual indicator indicating that movement direction of the ultrasound probe relative to the ultrasound image may be displayed.

18 Claims, 11 Drawing Sheets

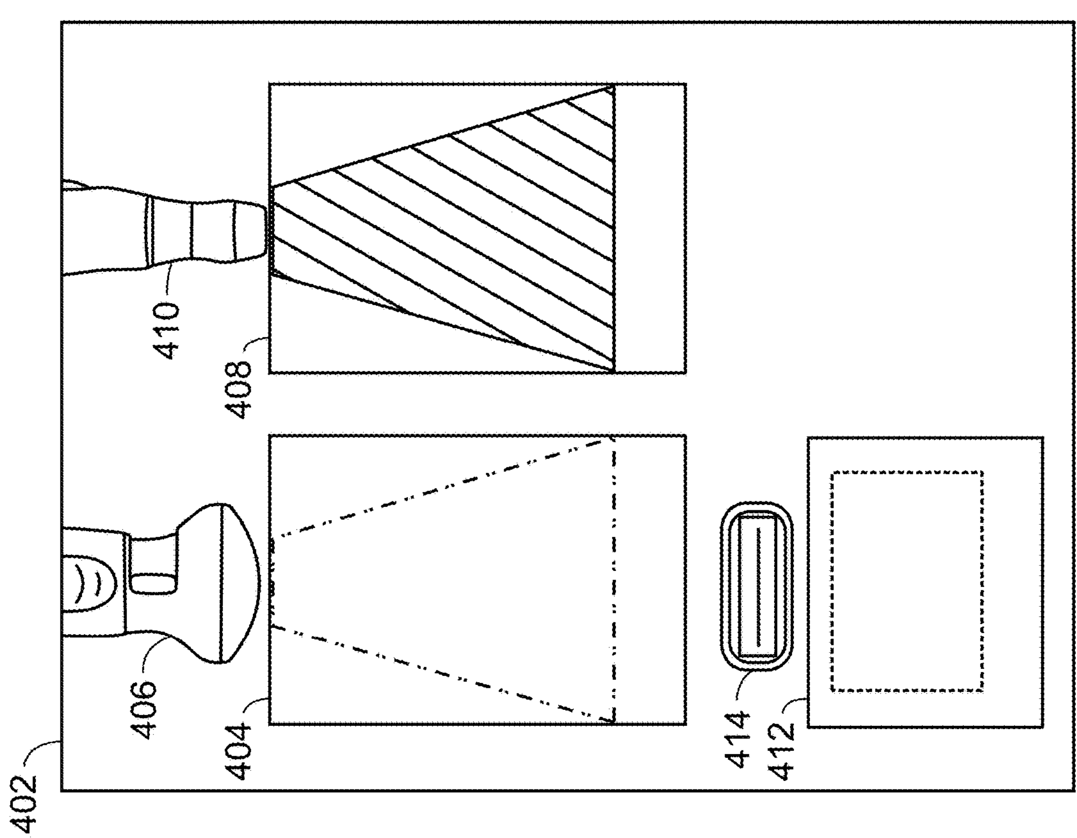
FIG. 4
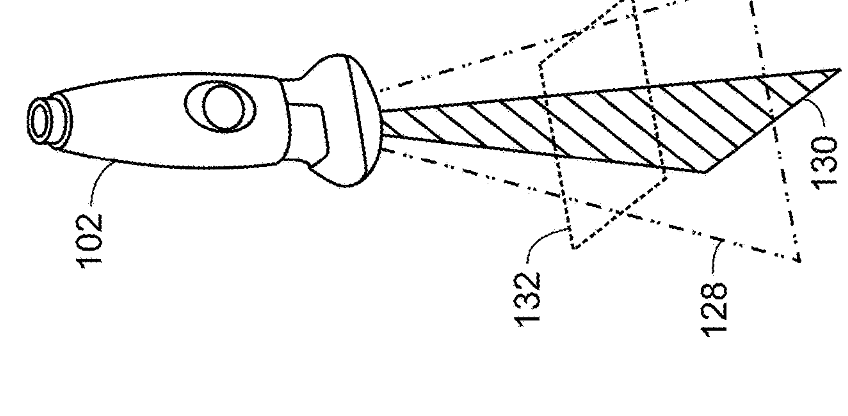

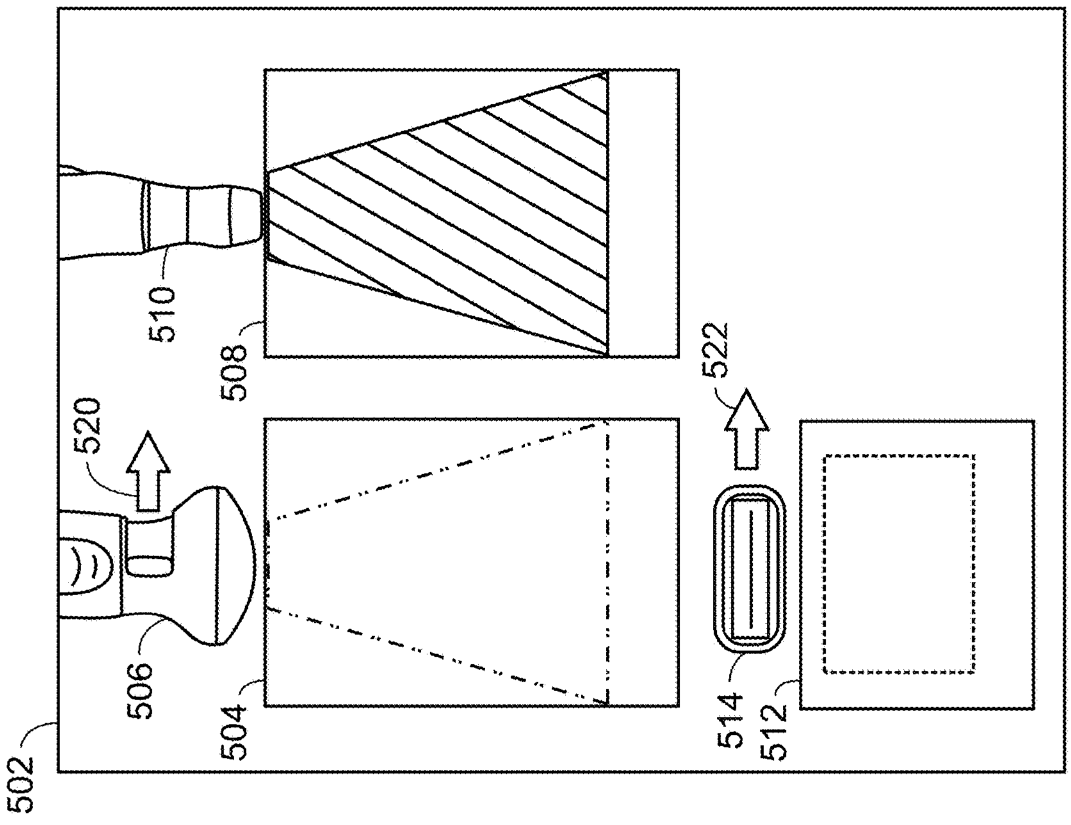
FIG. 5
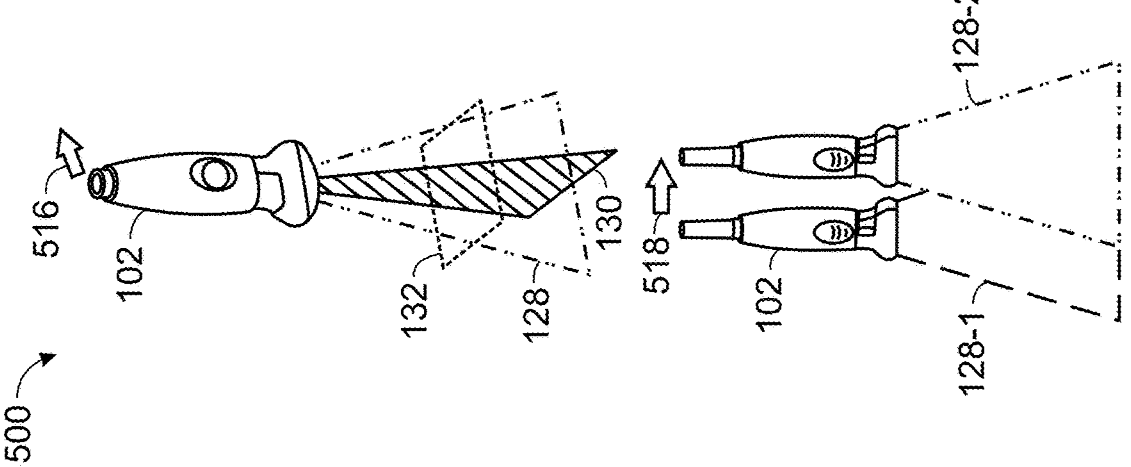

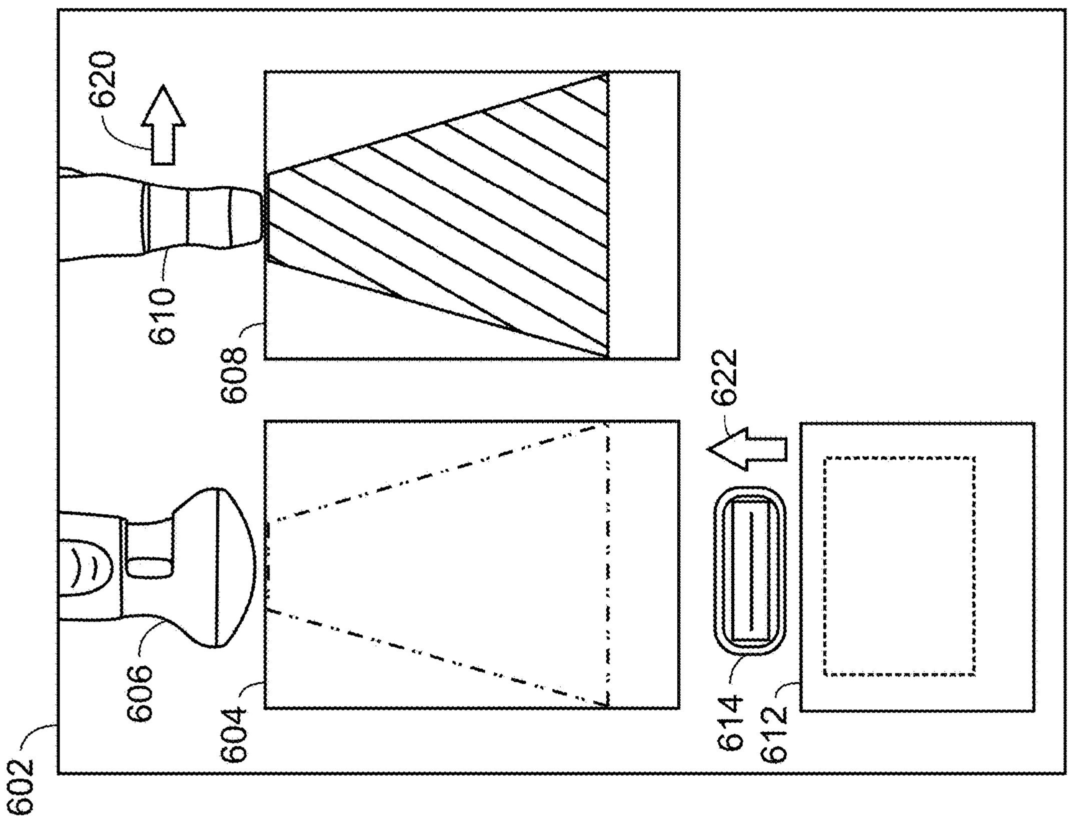
FIG. 6
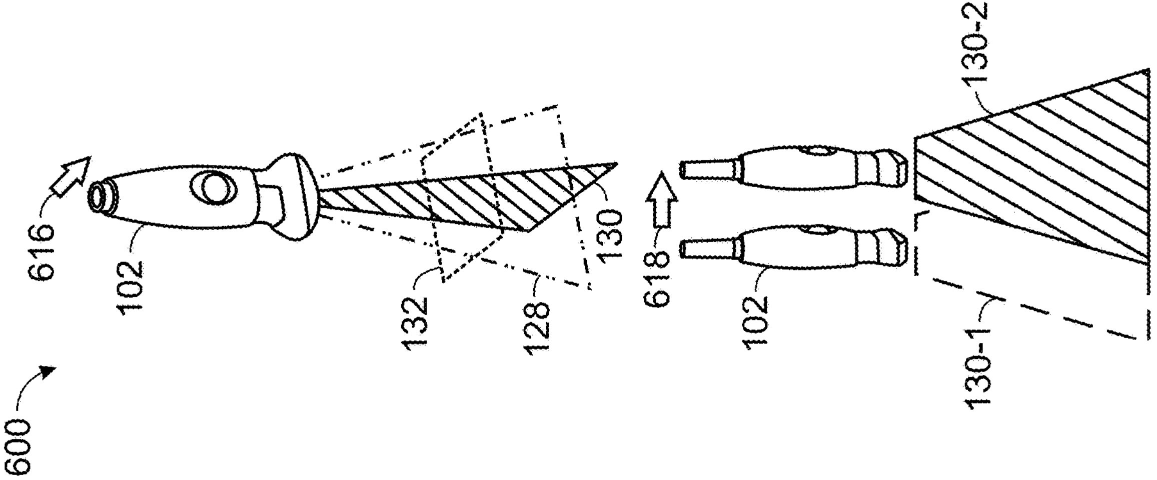

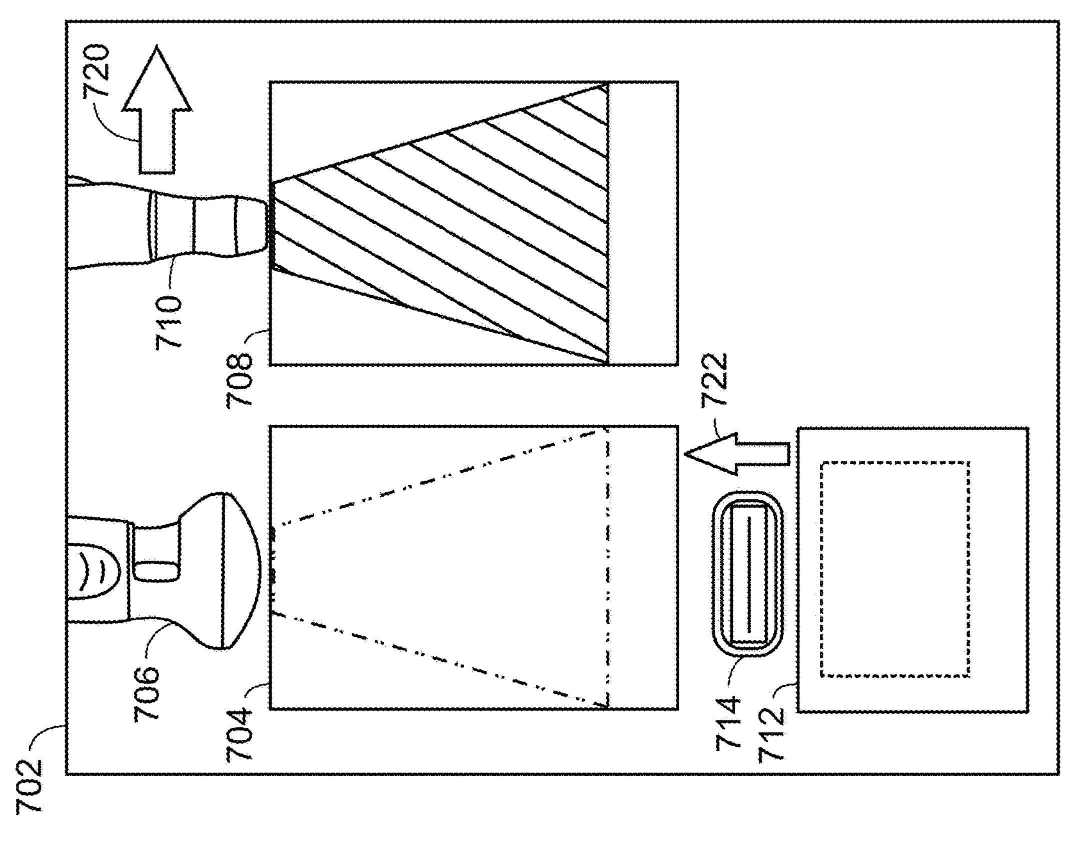
FIG. 7
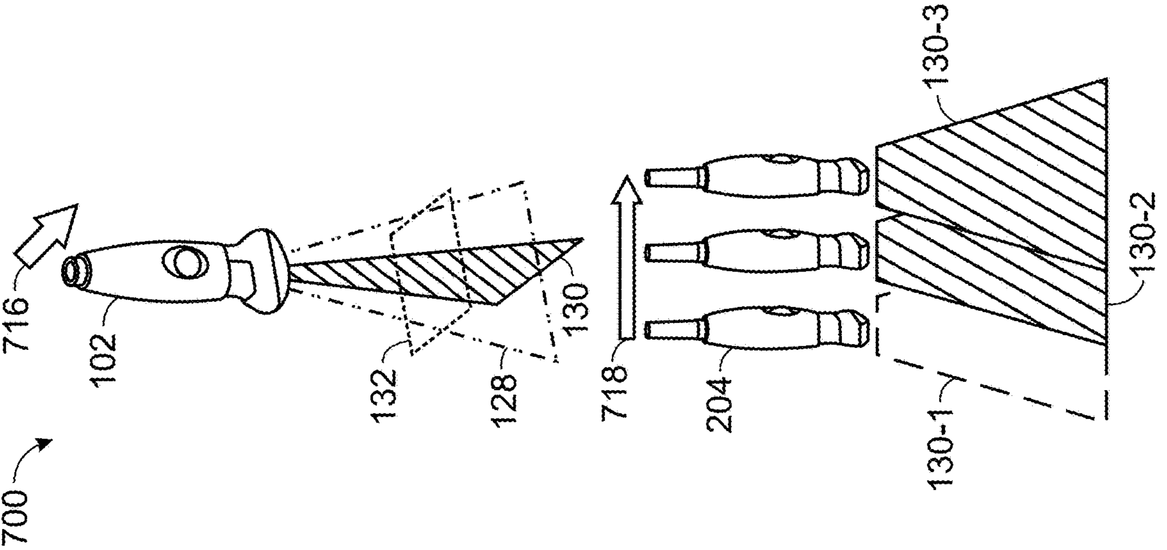

SYSTEM AND METHOD FOR DISPLAYING A VISUAL INDICATOR THAT INDICATES A MOVEMENT DIRECTION OF AN ULTRASOUND PROBE RELATIVE TO AN ULTRASOUND IMAGE

TECHNICAL FIELD

The present disclosure relates, generally, to displaying ultrasound images corresponding to scan planes of an ultrasound probe. More specifically, the present disclosure relates to a user interface for displaying ultrasound images.

BACKGROUND

An ultrasound probe may include multiple scan planes that are positioned relative to the ultrasound probe. For example, an ultrasound probe may include an "A-plane" that is parallel to a longitudinal axis of the ultrasound probe, a "B-plane" that is parallel to the longitudinal axis of the ultrasound probe and orthogonal to the A-plane, and a "C-plane" that is perpendicular to the longitudinal axis of the ultrasound probe and orthogonal to each of the A-plane and the B-plane.

The ultrasound probe may acquire ultrasound data corresponding to each scan plane, and provide the ultrasound data to an ultrasound system for imaging. For example, an ultrasound system may generate respective ultrasound images corresponding to the scan planes. The ultrasound system may simultaneously display the respective ultrasound images on a display. A viewer of the ultrasound images might find this type of display to be non-intuitive. That is, the viewer might not readily understand a relationship between a spatial position of the ultrasound probe and the ultrasound images. For instance, if the viewer desires to acquire ultrasound images of a region of interest that is located to a particular side of an imaged region in an ultrasound image, the viewer might not understand what direction in which to move the ultrasound probe to acquire ultrasound images of the desired region of interest. This issue may be exacerbated in the situation where multiple ultrasound images corresponding to multiple scan planes are simultaneously displayed.

Accordingly, the viewer might incorrectly or non-efficiently manipulate the ultrasound probe in an attempt to acquire ultrasound images of a particular region of interest. This incorrect or non-efficient manipulation may consume resources of the ultrasound system, prolong the duration of the scanning, reduce patient comfort, or the like, which might prove deleterious during interventional procedures.

SUMMARY

This summary introduces concepts that are described in more detail in the detailed description. It should not be used to identify essential features of the claimed subject matter, nor to limit the scope of the claimed subject matter.

In an aspect, a method may include receiving, from an ultrasound probe, ultrasound data corresponding to a scan plane of the ultrasound probe; generating an ultrasound image corresponding to the scan plane of the ultrasound probe using the ultrasound data; displaying the ultrasound image corresponding to the scan plane of the ultrasound probe; displaying, in relation to the ultrasound image, a representation of the ultrasound probe that is oriented relative to the scan plane corresponding to the ultrasound image; determining a movement direction of the ultrasound probe relative to the ultrasound image; and displaying, in relation to the representation of the ultrasound probe, a visual indicator that indicates the movement direction of the ultrasound probe relative to the ultrasound image.

In another aspect, a device may include a memory configured to store instructions; and one or more processors configured to execute the instructions to perform operations comprising: receiving, from an ultrasound probe, ultrasound data corresponding to a scan plane of the ultrasound probe; generating an ultrasound image corresponding to the scan plane of the ultrasound probe using the ultrasound data; displaying the ultrasound image corresponding to the scan plane of the ultrasound probe; displaying, in relation to the ultrasound image, a representation of the ultrasound probe that is oriented relative to the scan plane corresponding to the ultrasound image; determining a movement direction of the ultrasound probe relative to the ultrasound image; and displaying, in relation to the representation of the ultrasound probe, a visual indicator that indicates the movement direction of the ultrasound probe relative to the ultrasound image.

In yet another aspect, a method may include receiving, from an ultrasound probe, ultrasound data corresponding to a scan plane of the ultrasound probe; generating an ultrasound image corresponding to the scan plane of the ultrasound probe using the ultrasound data; displaying the ultrasound image corresponding to the scan plane of the ultrasound probe; determining a movement direction of the ultrasound probe relative to the ultrasound image; and displaying a visual indicator that indicates the movement direction of the ultrasound probe relative to the ultrasound image.

BRIEF DESCRIPTION OF DRAWINGS

FIG. 4 is a diagram of an example user interface for displaying a visual indicator that indicates a movement direction of an ultrasound probe relative to an ultrasound image.

FIG. 5 is a diagram of an example user interface for displaying a visual indicator that indicates a movement direction of an ultrasound probe relative to an ultrasound image.

FIG. 6 is a diagram of an example user interface for displaying a visual indicator that indicates a movement direction of an ultrasound probe relative to an ultrasound image.

FIG. 7 is a diagram of an example user interface for displaying a visual indicator that indicates a movement direction of an ultrasound probe relative to an ultrasound image.

DETAILED DESCRIPTION

As described above, an ultrasound system may simultaneously display multiple ultrasound images corresponding to respective scan planes of an ultrasound probe. Further, as described above, a viewer of the ultrasound images might find this type of display to be non-intuitive. That is, the viewer might not readily understand a relationship between a spatial position of the ultrasound probe and the ultrasound images. Accordingly, the viewer might incorrectly or non-efficiently manipulate the ultrasound probe in an attempt to acquire ultrasound images of a particular region of interest. This incorrect or non-efficient manipulation may consume resources of the ultrasound system, prolong the duration of the scanning, reduce patient comfort, or the like, which might prove deleterious during interventional procedures.

Some embodiments of the present disclosure provide an ultrasound system that determines a movement direction of an ultrasound probe relative to an ultrasound image, and displays a visual indicator that indicates the movement direction of the ultrasound probe relative to the ultrasound image. By viewing the visual indicator, a viewer of the ultrasound image may quickly and efficiently ascertain the spatial relationship between the ultrasound probe and the ultrasound image. Further, the viewer may correctly, or more efficiently, manipulate the ultrasound probe to acquire ultrasound images of a region of interest. In this way, some embodiments of the present disclosure conserve resources of the ultrasound system, reduce the duration of the scanning, or the like, which might improve patient safety and outcomes during interventional procedures.

Figure 1:
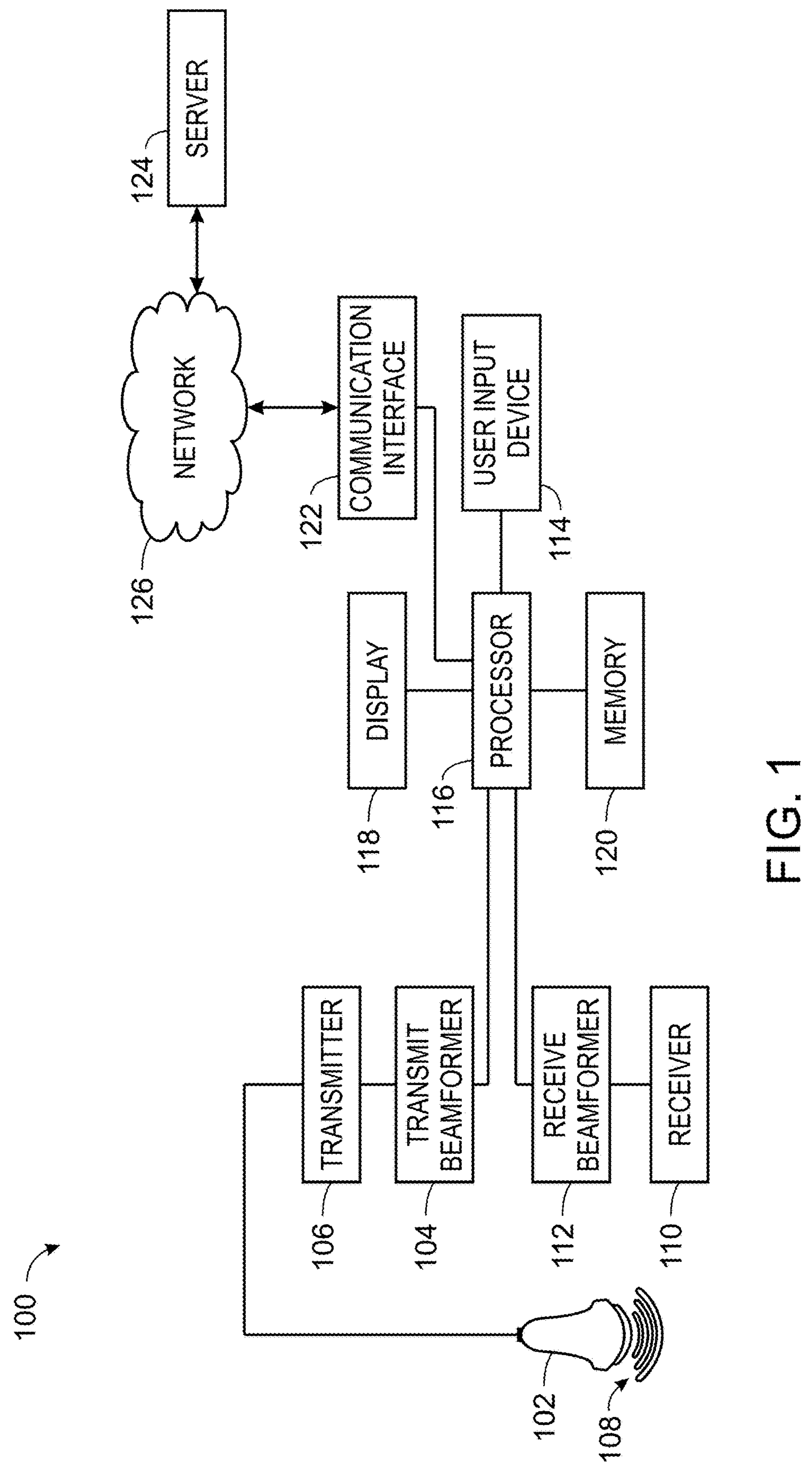
FIG. 1 is a diagram of an ultrasound system for displaying a visual indicator that indicates a movement direction of an ultrasound probe relative to an ultrasound image.

FIG. 1 is a diagram of an ultrasound system 100 for displaying a visual indicator that indicates a movement direction of an ultrasound probe 102 relative to an ultrasound image. As shown in FIG. 1, the ultrasound system 100 may include an ultrasound probe 102, a transmit beamformer 104, a transmitter 106, elements 108, a receiver 110, a receive beamformer 112, a user input device 114, a processor 116, a display 118, a memory 120, and a communication interface 122. The foregoing components may be connected via wired or wireless connections.

The ultrasound probe 102 may be configured to acquire ultrasound data. For example, the ultrasound probe 102 may be a linear probe, a phase array probe, a curved linear probe coupled with a position tracking system, a mechanically steered linear array transducer, a phased array transducer, a curved linear array transducer, an electronically steered 2D transducer array, an electronic 3D (e3D) probe, an electronic 4d (e4D) probe, a low profile wearable patch version of any of the foregoing probes, or the like. According to an embodiment, the ultrasound probe 102 may be configured to generate ultrasound signals, emit the ultrasound signals towards a region of interest of a subject, receive echo ultrasound signals that are back-scattered from the region of interest of the subject, generate ultrasound data based on the echo ultrasound signals, and output the ultrasound data. The region of interest may be any region of the anatomy of a subject. The subject may be a person, an animal, a phantom, or the like.

The transmit beamformer 104 may be configured to apply delay times to electrical signals provided to the elements 108 to focus corresponding ultrasound signals at the region of interest. The transmitter 106 may be configured to transmit electrical signals to the elements 108 to drive the elements 108 to emit ultrasound signals towards the region of interest. The elements 108 may be configured to receive the electrical signals from the transmitter 106, convert the electrical signals into ultrasound signals, and emit the ultrasound signals towards the region of interest. The elements 108 may be configured to receive echo ultrasound signals that are back-scattered by the region of interest, convert the echo ultrasound signals into electrical signals, and provide the electrical signals to the receiver 110. The receiver 110 may be configured to receive electrical signals from the elements 108, and provide the electrical signals to the receive beamformer 112. The receive beamformer 112 may apply delay times to the electrical signals received from the elements 108.

The user input device 114 may be configured to receive a user input, and provide the user input to the processor 116. For example, the user input device 114 may be a touch screen display, a keyboard, a keypad, a mouse, a button, a switch, a microphone, or the like. Additionally, or alternatively, the user input device 114 may be configured to sense information. For example, the user input device 114 may sense information from an electro-magnetic positioning system, an inertial measurement system, an accelerometer, a gyroscope, an actuator, or the like.

The processor 116 may be configured to perform the operations as described herein. For example, the processor 116 may be a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or the like. The processor 116 may be implemented in hardware, firmware, or a combination of hardware and software. The processor 116 may include one or more processors 116 configured to perform the operations described herein. For example, a single processor 116 may be configured to perform all of the operations described herein. Alternatively, multiple processors 116, collectively, may be configured to perform all of the operations described herein, and each of the multiple processors 116 may be configured to perform a subset of the operations descried herein. For example, a first processor 116 may perform a first subset of the operations described herein, a second processor 116 may be configured to perform a second subset of the operations described herein, etc.

The processor 116 may be configured to control the ultrasound probe 102 to acquire ultrasound data. The processor 116 may be configured to control which of the elements 108 are active, and control the shape of a beam emitted from the ultrasound probe 102. The processor 116 may control the ultrasound probe 102 to acquire ultrasound data correspond to a scan plane of the ultrasound probe 102. The ultrasound probe 102 may include one or more scan planes. For example, the ultrasound probe 102 may include a first scan plane that is parallel to the longitudinal axis of the ultrasound probe 102, a second scan plane that is parallel to the transverse axis of the ultrasound probe 102 and perpendicular to the first scan plane, and a third scan plane that is perpendicular to the longitudinal axis of the ultrasound probe 102. It should be understood that the ultrasound probe 102 may include any number of scan planes having any spatial configurations.

The processor 116 may generate ultrasound images for display. For example, the processor 116 may generate B-mode images, color Doppler images, M-mode images, color M-mode images, or the like. The ultrasound images may be 4D images, 3D images, 2D images, single plane images, bi-plane images, three-plane images, multi-plane images, or the like. The processor 116 may generate an ultrasound image correspond to a scan plane of the ultrasound probe 102. For example, the processor 116 may generate a first ultrasound image corresponding to a first scan plane that is parallel to the longitudinal axis of the ultrasound probe 102, generate a second ultrasound image corresponding to a second scan plane that is parallel to the longitudinal axis of the ultrasound probe 102 and perpendicular to the first scan plane, and generate a third ultrasound image corresponding to a third scan plane that is perpendicular to the longitudinal axis of the ultrasound probe 102. It should be understood that the processor 116 may generate any number of ultrasound images corresponding to any number of scan planes having any spatial configurations.

The display 118 may be configured to display information. For example, the display 118 may be a monitor, a light-emitting diode (LED) display, a cathode ray tube, a projector display, a touchscreen, tablet computer, mobile phone, or the like. The display 118 may display a user interface that includes an ultrasound image corresponding to a scan plane of the ultrasound probe 102. Additionally, the display 118 may display a representation of the ultrasound probe 102 that is oriented relative to the scan plane corresponding to the ultrasound image. Additionally, or alternatively, the display 118 may display a visual indicator that indicates a movement direction of the ultrasound probe 102 relative to the ultrasound image. The display 118 may display the visual indicator in relation to the representation of the ultrasound probe 102. The processor 116 may generate the visual indicator based on a movement direction of the ultrasound probe 102. Additionally, the processor 116 may generate the visual indicator based on a movement magnitude of the ultrasound probe 102. For example, the processor 116 may generate the visual indicator based on a velocity, an acceleration, a movement distance, or the like. The generated visual indicator may reflect the movement magnitude.

The display 118 may display ultrasound images based on the ultrasound data in real-time. For example, the display 118 may display the ultrasound images within one second, two seconds, five seconds, etc., of the ultrasound data being acquired by the ultrasound probe 102.

The memory 120 may be configured to store information and/or instructions for use by the processor 116. The memory 120 may be a non-transitory computer-readable medium. For example, the memory 120 may be a random access memory (RAM), a read only memory (ROM), a flash memory, a magnetic memory, an optical memory, or the like. The memory 120 may be configured to store instructions that, when executed by the processor 116, cause the processor 116 to perform the operations described herein.

The communication interface 122 may be configured to enable the processor 116 to communicate with other systems, such as via a wired connection, a wireless connection, or a combination of wired and wireless connections. For example, the communication interface 122 may include an Ethernet interface, an optical interface, a coaxial interface, an infrared interface, a radio frequency (RF) interface, a universal serial bus (USB) interface, a wireless fidelity (Wi-Fi) interface, a cellular network interface, or the like.

The server 124 may be configured to provide information to the processor 116. For example, the server 124 may be a cloud server, a database server, or the like. The server 124 may provide a model of the ultrasound probe 102 to the ultrasound system 100. For example, the server 124 may store various models of various ultrasound probes 102, and map the various models to respective probe identifiers of the ultrasound probes 102. The server 124 may provide a model to the processor 116 based on a probe identifier of an ultrasound probe 102 connected to the processor 116.

The network 126 may permit communication between the ultrasound system 100 and external systems and/or devices. For example, the network 126 may be a local area network (LAN), a wide area network (WAN), a metropolitan area network (MAN), a cellular network, a private network, an ad hoc network, an intranet, the Internet, a fiber optic-based network, a wired network, a wireless network, or the like, and/or a combination of these or other types of networks.

Figure 3:
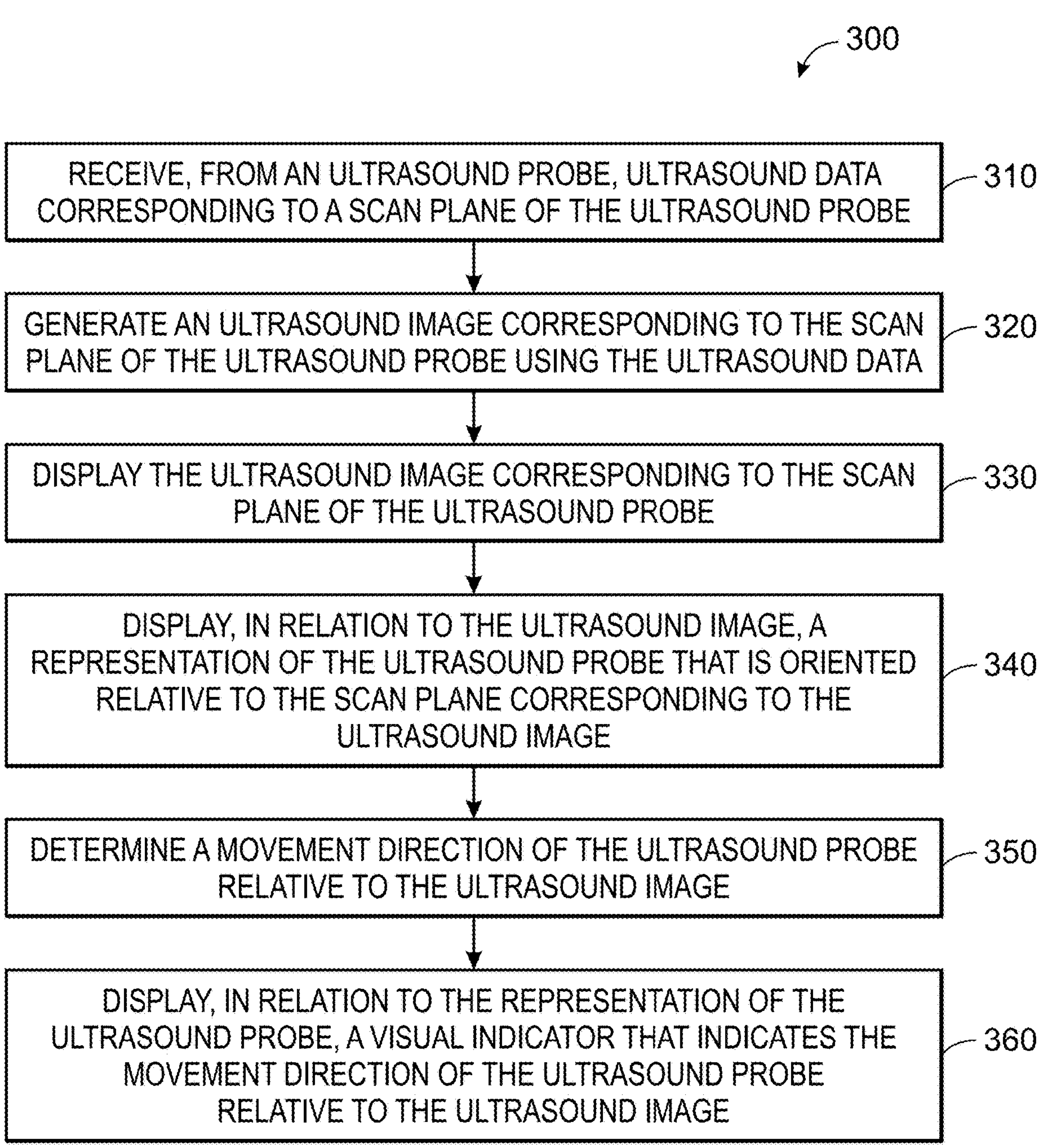
FIG. 3 is a flowchart of an example process for displaying a visual indicator that indicates a movement direction of an ultrasound probe relative to an ultrasound image.

The number and arrangement of the components of the ultrasound system 100 shown in FIG. 3 are provided as an example. In practice, the ultrasound system 100 may include additional components, fewer components, different components, or differently arranged components than those shown in FIG. 3. Additionally, or alternatively, a set of components (e.g., one or more components) of the ultrasound system 100 may perform one or more functions described as being performed by another set of components of the ultrasound system 100.

Figure 2:
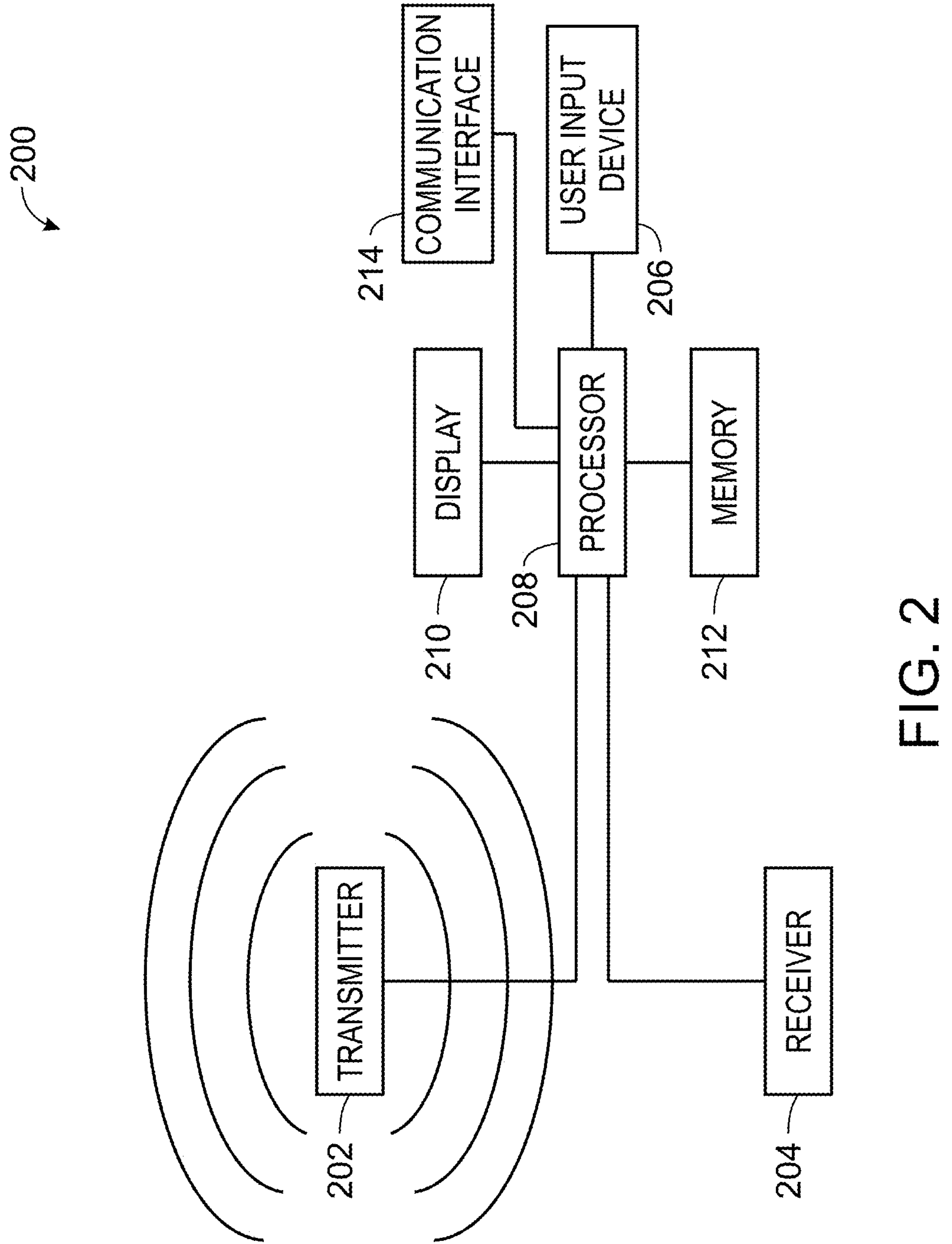
FIG. 2 is a diagram of a tracking system for acquiring tracking data of an ultrasound probe.

FIG. 2 is a diagram of a tracking system 200 for acquiring tracking data of an ultrasound probe 102. As shown in FIG. 2, the tracking system 200 may include a transmitter 202, a receiver 204, a user input device 206, a processor 208, a display 210, a memory 212, and a communication interface 214.

The transmitter 202 may be configured to generate a magnetic field. The receiver 204 may be configured to output a signal in response to the magnetic field generated by the transmitter 202. The processor 208 may receive the output signal from the receiver 204, and acquire tracking data that identifies a position and/or an orientation of the receiver 204. According to an embodiment, the receiver 204 may be attached to the ultrasound probe 102 to track a position and/or an orientation of the ultrasound probe 102. Alternatively, the receiver 204 may be attached to an interventional device to track a position and/or an orientation of the interventional device. The interventional device may be a catheter, a needle, or the like.

The user input device 206 may be configured to receive a user input, and provide the user input to the processor 208. For example, the user input device 206 may be a touch screen display, a keyboard, a keypad, a mouse, a button, a switch, a microphone, or the like. Additionally, or alternatively, the user input device 206 may be configured to sense information. For example, the user input device 206 may sense information from an electro-magnetic positioning system, an inertial measurement system, an accelerometer, a gyroscope, an actuator, or the like.

The processor 208 may be configured to perform the operations as described herein. For example, the processor 208 may be a CPU, a GPU, an APU, a microprocessor, a microcontroller, a DSP, an FPGA, an ASIC, or the like. The processor 208 may be implemented in hardware, firmware, or a combination of hardware and software. The processor 208 may include one or more processors 208 configured to perform the operations described herein. For example, a single processor 208 may be configured to perform all of the operations described herein. Alternatively, multiple processors 208, collectively, may be configured to perform all of the operations described herein, and each of the multiple processors 208 may be configured to perform a subset of the operations descried herein. For example, a first processor 208 may perform a first subset of the operations described herein, a second processor 208 may be configured to perform a second subset of the operations described herein, etc.

The processor 208 may be configured to control the transmitter 202 to acquire tracking data. The processor 208 may be configured to control excitations of the transmitter 202 to generate a magnetic field. The processor 208 may acquire tracking data based on controlling the transmitter 202.

The display 210 may be configured to display information. For example, the display 210 may be a monitor, an LED display, a cathode ray tube, a projector display, a touchscreen, tablet computer, mobile phone, or the like. The display 210 may display the tracking data in real-time. For example, the display 210 may display the tracking data within one second, two seconds, five seconds, etc., of the tracking data being acquired.

The memory 212 may be configured to store information and/or instructions for use by the processor 208. The memory 212 may be a non-transitory computer-readable medium. For example, the memory 212 may be a RAM, a ROM, a flash memory, a magnetic memory, an optical memory, or the like. The memory 212 may be configured to store instructions that, when executed by the processor 208, cause the processor 208 to perform the operations described herein.

The communication interface 214 may be configured to enable the processor 208 to communicate with other systems, such as via a wired connection, a wireless connection, or a combination of wired and wireless connections. For example, the communication interface 214 may include an Ethernet interface, an optical interface, a coaxial interface, an infrared interface, an RF interface, a USB interface, a Wi-Fi interface, a cellular network interface, or the like.

The number and arrangement of the components of the tracking system 200 shown in FIG. 2 are provided as an example. In practice, the tracking system 200 may include additional components, fewer components, different components, or differently arranged components than those shown in FIG. 2. Additionally, or alternatively, a set of components (e.g., one or more components) of the tracking system 200 may perform one or more functions described as being performed by another set of components of the tracking system 200.

Although FIG. 2 depicts the tracking system 200 as being an electromagnetic tracking system, it should be understood that the embodiments herein are applicable to other types of tracking systems, such as optical tracking systems, acoustic tracking systems, or the like.

FIG. 3 is a flowchart of an example process 300 for displaying a visual indicator that indicates a movement direction of an ultrasound probe relative to an ultrasound image.

As shown in FIG. 3, the process 300 may include receiving, from an ultrasound probe, ultrasound data corresponding to a scan plane of the ultrasound probe (operation 310). For example, the processor 116 may receive, from the ultrasound probe 102, ultrasound data corresponding to a scan plane of the ultrasound probe 102.

The processor 116 may control the ultrasound probe 102 to acquire ultrasound data corresponding to a scan plane of the ultrasound probe 102, and receive the ultrasound data from the ultrasound probe 102 based on controlling the ultrasound probe 102. The scan plane may be any scan plane of the ultrasound probe 102. Further, the scan plane may have a predetermined spatial relationship to the ultrasound probe 102. For example, the scan plane may be an A plane that is parallel to a longitudinal axis of the ultrasound probe 102, a B plane that is parallel to the longitudinal axis of the ultrasound probe 102 and that is orthogonal to the A plane, a C plane of the ultrasound probe 102 that is perpendicular to the longitudinal axis of the ultrasound probe 102, or the like. The processor 116 may control the ultrasound probe 102 to acquire ultrasound data corresponding to n (e.g., 1, 2, 3, etc.) scan planes of the ultrasound probe 102.

As further shown in FIG. 3, the process 300 may include generating an ultrasound image corresponding to the scan plane of the ultrasound probe using the ultrasound data (operation 320). For example, the processor 116 may generate an ultrasound image corresponding to the scan plane of the ultrasound probe 102 using the ultrasound data. The ultrasound image may include a B-mode image, a color Doppler image, an M-mode image, a color M-mode image, any combination of modes, or the like.

As further shown in FIG. 3, the process 300 may include displaying the ultrasound image corresponding to the scan plane of the ultrasound probe (operation 330). For example, the processor 116 may display the ultrasound image via the display 118.

As further shown in FIG. 3, the process 300 may include displaying, in relation to the ultrasound image, a representation of the ultrasound probe that is oriented relative to the scan plane corresponding to the ultrasound image (operation 340). For example, the processor 116 may display, in relation to the ultrasound image, a representation of the ultrasound probe 102 that is orientated relative to the scan plane corresponding to the ultrasound image.

The representation of the ultrasound probe 102 may be a representation of the ultrasound probe 102 that depicts a spatial relationship between the ultrasound probe 102 and the scan plane of the ultrasound image. For example, if the scan plane is parallel to a longitudinal axis of the ultrasound probe 102 and perpendicular to a particular side of the ultrasound probe 102, then the representation may depict the particular side of the ultrasound probe 102. In this way, a viewer of the display 118 may readily and quickly assess the spatial relationship between the ultrasound probe 102 and the ultrasound image.

According to an embodiment, the processor 116 may generate the representation of the ultrasound probe 102 to correspond to the particular ultrasound probe 102. For example, the processor 116 may generate the representation of the ultrasound probe 102 using a model (e.g., a software rendered model) of the ultrasound probe 102 that is determined based on a probe identifier of the ultrasound probe 102, as described below in more detail in connection with FIG. 11. Alternatively, the processor 116 may generate the representation of the ultrasound probe 102 to correspond to a generic ultrasound probe 102. For example, the processor 116 may generate the representation based on predetermined information that identifies the spatial relationship between the ultrasound probe 102 and the scan plane of the ultrasound image.

As further shown in FIG. 3, the process 300 may include determining a movement direction of the ultrasound probe relative to the ultrasound image (operation 350). For example, the processor 116 may determine a movement direction of the ultrasound probe 102 relative to the ultrasound image.

According to an embodiment, the processor 116 may determine the movement direction of the ultrasound probe 102 relative to the ultrasound image using a motion estimation technique, as described below in more detail in connection with FIG. 8. Additionally, or alternatively, the processor 116 may determine the movement direction of the ultrasound probe 102 relative to the ultrasound image using motion data acquired from the ultrasound probe 102, as described below in more detail in connection with FIG. 9. Additionally, or alternatively, the processor 116 may determine the movement direction of the ultrasound probe 102 relative to the ultrasound image using tracking data acquired from the tracking system 200, as described below in more detail in connection with FIG. 10.

According to an embodiment, the processor 116 may determine the movement direction of the ultrasound probe 102 relative to the ultrasound image (e.g., up, down, left, right, rotate up, rotate down, rotate left, rotate right, etc.). Additionally, or alternatively, the processor 116 may determine a velocity of the ultrasound probe 102, an acceleration of the ultrasound probe 102, a movement distance of the ultrasound probe 102, or the like.

As further shown in FIG. 3, the process 300 may include displaying, in relation to the representation of the ultrasound probe, a visual indicator that indicates the movement direction of the ultrasound probe relative to the ultrasound image (operation 360). For example, the processor 116 may display a visual indicator that indicates the movement direction of the ultrasound probe relative to the ultrasound image via the display 118. The visual indicator may be any visual indicator that indicates the movement direction of the ultrasound probe relative to the ultrasound image.

According to an embodiment, the visual indicator may be an icon that identifies the movement direction of the ultrasound probe 102 relative to the ultrasound image. For example, the icon may be an arrow, a circle, a semi-circle, a square, a line, or the like. As an example, if the movement direction of the ultrasound probe 102 is to the right of the ultrasound image, then the visual indicator may be an icon that indicates "right."

Alternatively, the visual indicator may be text that identifies the movement direction of the ultrasound probe 102 relative to the ultrasound image. For example, the text may be "right," "left," "up," "down," or the like. As an example, if the movement direction of the ultrasound probe 102 is to the right of the ultrasound image, then the visual indicator may be text that indicates "right."

Alternatively, the visual indicator may be a legend that identifies the movement direction. The legend may include components that designate particular directions. For example, the legend may be a compass, a map, a graphic, or the like. A particular component of the legend may be highlighted. As an example, if the movement direction of the ultrasound probe 102 is to the right of the ultrasound image, then the visual indicator may be a component that is highlighted, emphasized, or the like.

Alternatively, the visual indicator may be a display effect of the ultrasound image that identifies the movement direction. For example, the display effect may be a transition, a shadow, a blur, a fade, or the like. As an example, if the movement direction of the ultrasound probe 102 is to the right of the ultrasound image, then the visual indicator may be a transition of the ultrasound image to the right.

According to an embodiment, the visual indicator may identify a magnitude of the movement of the ultrasound probe 102 relative to the ultrasound image. For example, the visual indicator may indicate a magnitude of a velocity of the ultrasound probe 102, a magnitude of an acceleration of the ultrasound probe 102, a magnitude of a movement distance of the ultrasound probe 102, or the like. According to an embodiment, the visual indicator may identify a magnitude of the movement based on a size of the visual indicator. For example, a larger visual indicator may indicate a greater magnitude than a relatively smaller visual indicator. Alternatively, the visual indicator may identify a magnitude of the movement based on a color of the visual indicator. For example, a red visual indicator may indicate a greater magnitude than a green visual indicator. Alternatively, the visual indicator may identify a magnitude of the movement based on a style of the visual indicator, a location of the visual indicator, a duration of the display of the visual indicator, a brightness of the visual indicator, a pattern of display of the visual indicator, or the like.

The processor 116 may generate a visual indicator, and control the display 118 to display the visual indicator. For example, the processor 116 may generate respective visual indicators for one or more ultrasound images corresponding to one or more scan planes of the ultrasound probe 102, and control the display 118 to display the one or more visual indicators. In this way, a viewer of the display 118 may quickly, efficiently, and readily ascertain how movement of the ultrasound probe 102 affects the ultrasound images.

According to an embodiment, the processor 116 may record the movement of the ultrasound probe 102 and store data related to the movement of the ultrasound probe 102. The display 118 may display the stored data after the acquisition of the ultrasound data.

FIG. 4 is a diagram 400 of an example user interface 402 for displaying a visual indicator that indicates a movement direction of an ultrasound probe 102 relative to an ultrasound image. As shown in FIG. 4, the ultrasound probe 102 may include a first scan plane 128, a second scan plane 130, and a third scan plane 132. The processor 116 may control the display 118 to display a user interface 402 including ultrasound images corresponding to the scan planes. For example, the user interface 402 may include a first ultrasound image 404 corresponding to the first scan plane 128. Further, the user interface 402 may include a first representation 406 of the ultrasound probe 102 that is oriented relative to the first scan plane 128 corresponding to the first ultrasound image 404. Further, the user interface 402 may include a second ultrasound image 408 corresponding to the second scan plane 130. Further, the user interface 402 may include a second representation 410 of the ultrasound probe 102 that is oriented relative to the second scan plane 130 corresponding to the second ultrasound image 408. Further, the user interface 402 may include a third ultrasound image 412 corresponding to the third scan plane 132. Further, the user interface 402 may include a third representation 414 of the ultrasound probe 102 that is oriented relative to the third scan plane 132 corresponding to the third ultrasound image 412.

FIG. 5 is a diagram 500 of an example user interface 502 for displaying a visual indicator that indicates a movement direction of an ultrasound probe 102 relative to an ultrasound image. As shown in FIG. 5, the ultrasound probe 102 may include a first scan plane 128, a second scan plane 130, and a third scan plane 132. The processor 116 may control the display 118 to display a user interface 502 including ultrasound images corresponding to the scan planes. For example, the user interface 502 may include a first ultrasound image 504 corresponding to the first scan plane 128. Further, the user interface 502 may include a first representation 506 of the ultrasound probe 102 that is oriented relative to the first scan plane 128 corresponding to the first ultrasound image 504. Further, the user interface 502 may include a second ultrasound image 508 corresponding to the second scan plane 130. Further, the user interface 502 may include a second representation 510 of the ultrasound probe 102 that is oriented relative to the second scan plane 130 corresponding to the second ultrasound image 508. Further, the user interface 502 may include a third ultrasound image 512 corresponding to the third scan plane 132. Further, the user interface 502 may include a third representation 514 of the ultrasound probe 102 that is oriented relative to the third scan plane 132 corresponding to the third ultrasound image 512. As shown by reference number 516, an operator of the ultrasound probe 102 may move the ultrasound probe 102 in a particular movement direction as indicated by the arrow designated by reference number 516. As shown by reference number 518, the movement may move the first scan plane 128 from a first position 128-1 to a second position 128-2. The user interface 502 may display a first visual indicator 520 that indicates the movement direction of the ultrasound probe 102 relative to the first ultrasound image 504. Further, the user interface 502 may display a second visual indicator 522 that indicates the movement direction of the ultrasound probe 102 relative to the third ultrasound image 512.

FIG. 6 is a diagram 600 of an example user interface 602 for displaying a visual indicator that indicates a movement direction of an ultrasound probe 102 relative to an ultrasound image. As shown in FIG. 6, the ultrasound probe 102 may include a first scan plane 128, a second scan plane 130, and a third scan plane 132. The processor 116 may control the display 118 to display a user interface 602 including ultrasound images corresponding to the scan planes. For example, the user interface 602 may include a first ultrasound image 604 corresponding to the first scan plane 128. Further, the user interface 602 may include a first representation 606 of the ultrasound probe 102 that is oriented relative to the first scan plane 128 corresponding to the first ultrasound image 604. Further, the user interface 602 may include a second ultrasound image 608 corresponding to the second scan plane 130. Further, the user interface 602 may include a second representation 610 of the ultrasound probe 102 that is oriented relative to the second scan plane 130 corresponding to the second ultrasound image 608. Further, the user interface 602 may include a third ultrasound image 612 corresponding to the third scan plane 132. Further, the user interface 602 may include a third representation 614 of the ultrasound probe 102 that is oriented relative to the third scan plane 132 corresponding to the third ultrasound image 612. As shown by reference number 616, an operator of the ultrasound probe 102 may move the ultrasound probe 102 in a particular movement direction as indicated by the arrow designated by reference number 616. As shown by reference number 618, the movement may move the second scan plane 130 from a first position 130-1 to a second position 130-2. The user interface 602 may display a first visual indicator 620 that indicates the movement direction of the ultrasound probe 102 relative to the second ultrasound image 608. Further, the user interface 602 may display a second visual indicator 622 that indicates the movement direction of the ultrasound probe 102 relative to the third ultrasound image 612.

FIG. 7 is a diagram 700 of an example user interface 702 for displaying a visual indicator that indicates a movement direction of an ultrasound probe 102 relative to an ultrasound image. As shown in FIG. 7, the ultrasound probe 102 may include a first scan plane 128, a second scan plane 130, and a third scan plane 132. The processor 116 may control the display 118 to display a user interface 702 including ultrasound images corresponding to the scan planes. For example, the user interface 702 may include a first ultrasound image 704 corresponding to the first scan plane 128. Further, the user interface 702 may include a first representation 706 of the ultrasound probe 102 that is oriented relative to the first scan plane 128 corresponding to the first ultrasound image 704. Further, the user interface 702 may include a second ultrasound image 708 corresponding to the second scan plane 130. Further, the user interface 702 may include a second representation 710 of the ultrasound probe 102 that is oriented relative to the second scan plane 130 corresponding to the second ultrasound image 708. Further, the user interface 702 may include a third ultrasound image 712 corresponding to the third scan plane 132. Further, the user interface 702 may include a third representation 714 of the ultrasound probe 102 that is oriented relative to the third scan plane 132 corresponding to the third ultrasound image 712. As shown by reference number 716, an operator of the ultrasound probe 102 may move the ultrasound probe 102 in a particular movement direction as indicated by the arrow designated by reference number 716. As shown by reference number 718, the movement may move the second scan plane 130 from a first position 130-1 to a second position 130-2 and a third position 130-3. The user interface 702 may display a first visual indicator 720 that indicates the movement direction of the ultrasound probe 102 relative to the second ultrasound image 708. Further, the user interface 702 may display a second visual indicator 722 that indicates the movement direction of the ultrasound probe 102 relative to the third ultrasound image 712. A magnitude of the movement of the ultrasound probe 102 relative to the second ultrasound image 708 may be greater than a threshold. In this case, the processor 116 may generate the first visual indicator 720 to have a size that is indicative of the magnitude of the movement being greater than the threshold.

Figure 8:
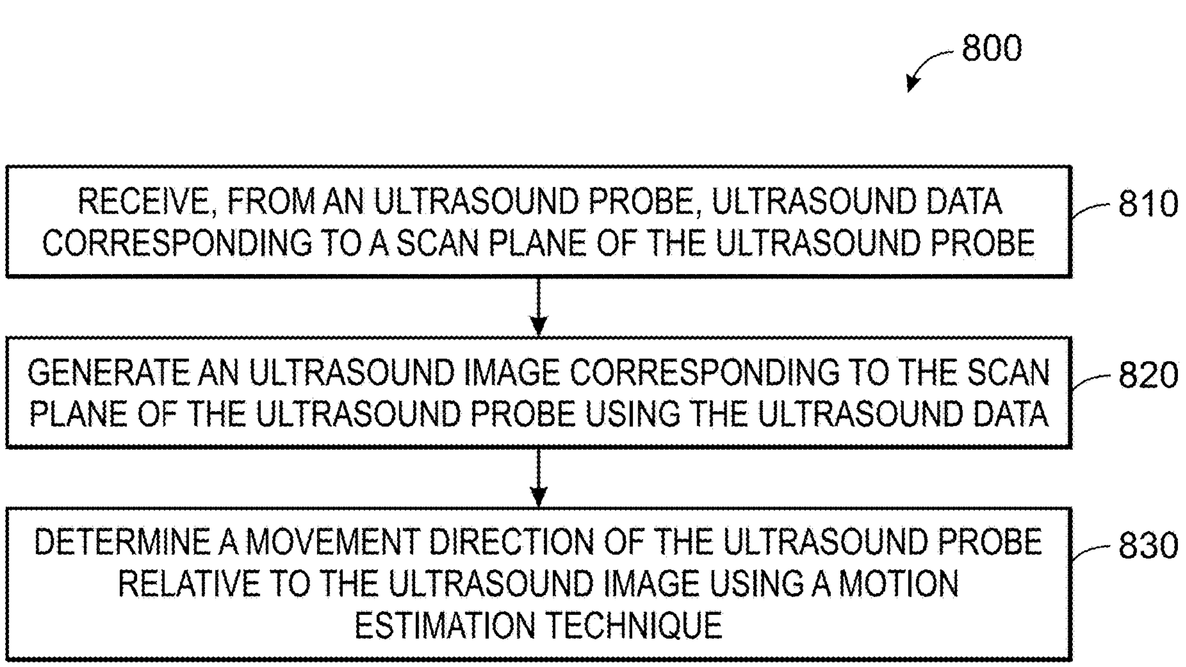
FIG. 8 is a flowchart of an example process for determining a movement direction of an ultrasound probe using a motion estimation technique.

FIG. 8 is a flowchart of an example process 800 for determining a movement direction of an ultrasound probe 102 using a motion estimation technique. As shown in FIG. 8, the process 800 may include receiving, from an ultrasound probe, ultrasound data corresponding to a scan plane of the ultrasound probe (operation 810). For example, the processor 116 may receive, from the ultrasound probe 102, ultrasound data corresponding to a scan plane of the ultrasound probe 102. As further shown in FIG. 8, the process 800 may include generating an ultrasound image corresponding to the scan plane of the ultrasound probe 102 using the ultrasound data (operation 820). For example, the processor 116 may generate an ultrasound image corresponding to the scan plane of the ultrasound probe 102 using the ultrasound data. As further shown in FIG. 8, the process 800 may include determining a movement direction of the ultrasound probe relative to the ultrasound image using a motion estimation technique (operation 830). For example, the processor 116 may determine a movement direction of the ultrasound probe 102 relative to the ultrasound image using a motion estimation technique.

According to an embodiment, the motion estimation technique may be a block-matching technique, a phase correlation technique, a pixel recursive technique, an optical flow technique, an image registration technique, a feature matching technique, or the like.

As a specific example, and according to an embodiment, the processor 116 may determine a lag value ($lag_x$) using the following function:

$$lag_x = \text{argmax}\left(I_{y_0}(n) * I_{y_0}(n-1)\right)$$

Here, * is cross correlation, $I_{d_0}(n)$ is an ultrasound image at time instance $t_n$, and $y_0$ is a fixed depth. The fixed depth may be at either a single line, or multiple lines for an improved estimate of lateral motion of the ultrasound image.

The processor 116 may determine a motion vector ($\vec{v}$(x, y)) with a known framerate using the following function:

$$\vec{v}(x, y) = (lag_x \cdot Fr, lag_y \cdot Fr),$$

Using two active scan planes ($I_a$(x, z, t), $I_b$(y, z, t)) that are orthogonal to each other, the processor 116 may determine the full 3D motion using the ultrasound images. Here, x, y, z represent physical coordinates, and t represents time.

From $I_a$, the processor 116 may determine velocity components: $\vec{v}_a$(x, z) as a function of time. Further, from $I_b$, the processor 116 may determine velocity components $\vec{v}_b$(y, z) as a function of time.

The processor 116 may determine 3D motion of the ultrasound probe 102 using the velocity components and the following function:

$$v(x, y, z, t) = \begin{pmatrix} v_a(x, t) \\ 0 \\ c_a \cdot v_a(z, t) \end{pmatrix} + \begin{pmatrix} 0 \\ v_b(x, t) \\ c_b \cdot v_b(z, t) \end{pmatrix}$$

Figure 9:
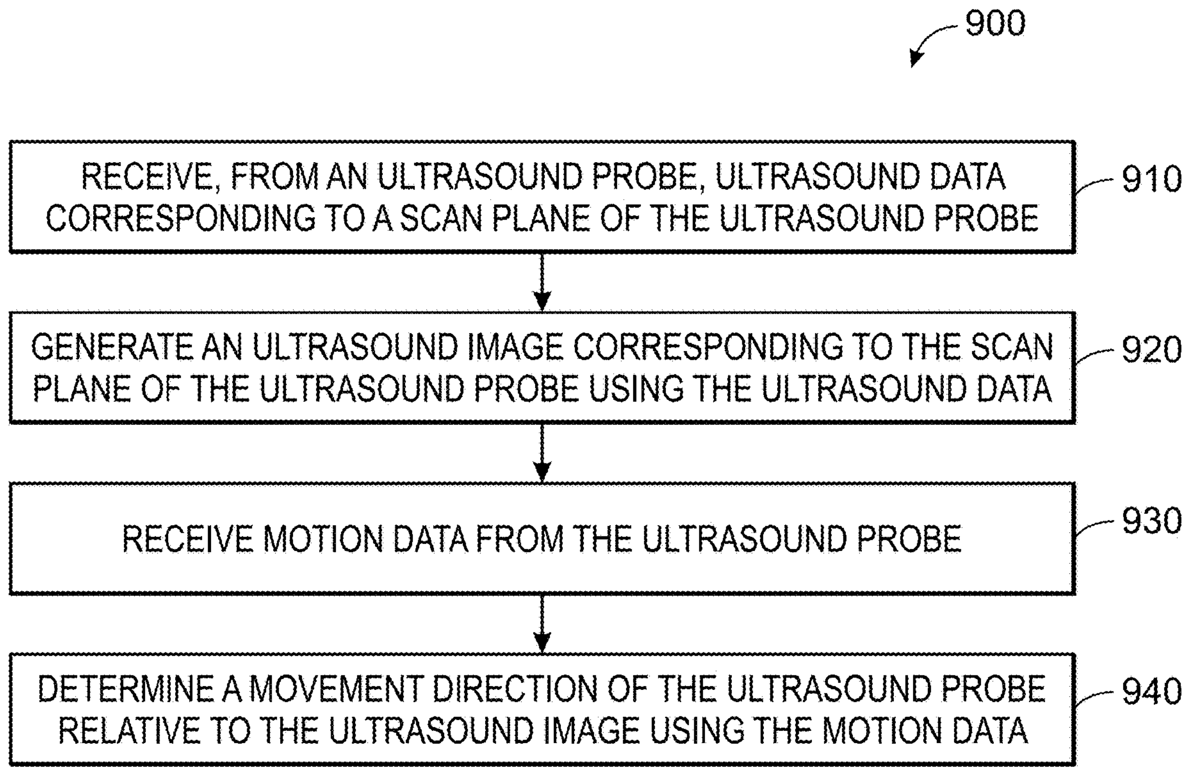
FIG. 9 is a flowchart of an example process for determining a movement direction of an ultrasound probe using motion data received from an ultrasound probe.

FIG. 9 is a flowchart of an example process 900 for determining a movement direction of an ultrasound probe 102 using motion data received from an ultrasound probe 102. As shown in FIG. 9, the process 900 may include receiving, from an ultrasound probe 102, ultrasound data corresponding to a scan plane of the ultrasound probe (operation 910). For example, the processor 116 may receive, from the ultrasound probe 102, ultrasound data corresponding to a scan plane of the ultrasound probe 102. As further shown in FIG. 9, the process 900 may include generating an ultrasound image corresponding to the scan plane of the ultrasound probe using the ultrasound data (operation 920). For example, the processor 116 may generate an ultrasound image corresponding to the scan plane of the ultrasound probe using the ultrasound data. As further shown in FIG. 9, the process 900 may include receiving motion data from the ultrasound probe (operation 930). For example, the processor 116 may receive motion data from the ultrasound probe 102. The motion data may be vector flow imaging (VFI) data, transverse oscillation tensor velocity imaging data, Doppler data, or the like. As further shown in FIG. 9, the process 900 may include determining a movement direction of the ultrasound probe relative to the ultrasound image using the motion data (operation 940).

Figure 10:
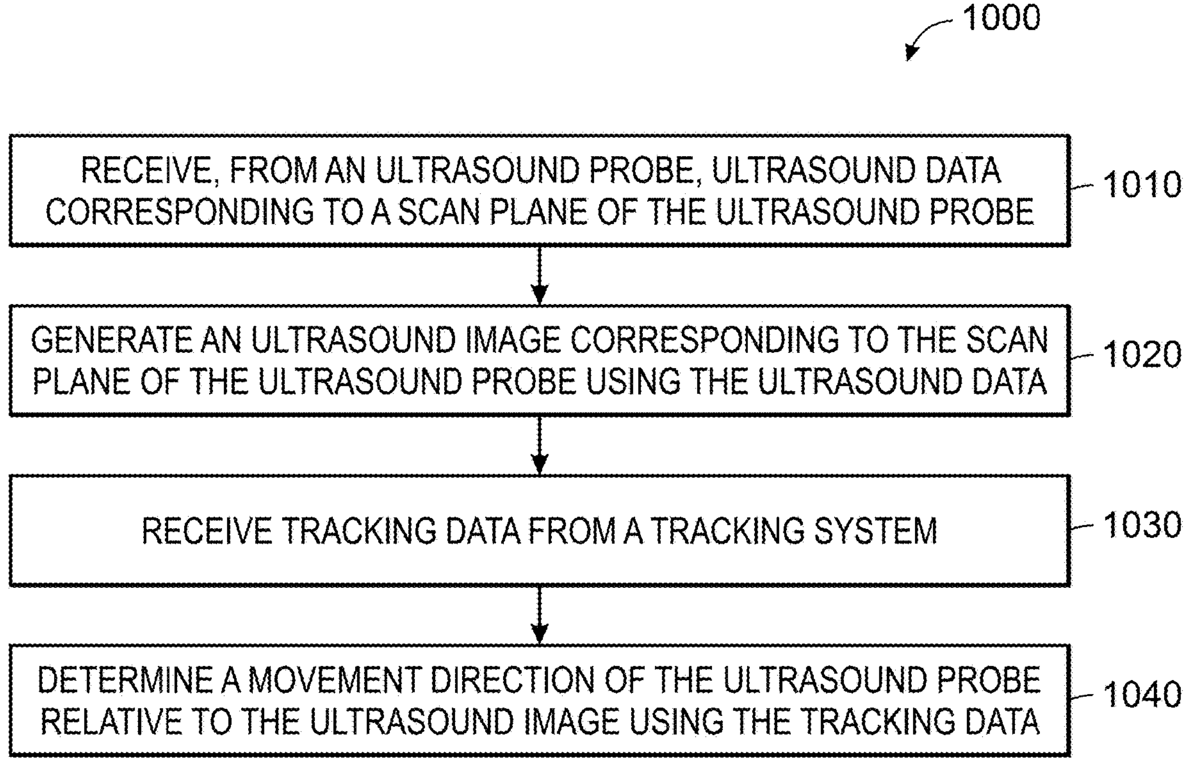
FIG. 10 is a flowchart of an example process for determining a movement direction of an ultrasound probe using tracking data received from a tracking system.

FIG. 10 is a flowchart of an example process 1000 for determining a movement direction of an ultrasound probe 102 using tracking data received from a tracking system 200. As shown in FIG. 10, the process 1000 may include receiving, from an ultrasound probe, ultrasound data corresponding to a scan plane of the ultrasound probe (operation 1010). For example, the processor 116 may receive, from the ultrasound probe 102, ultrasound data corresponding to a scan plane of the ultrasound probe 102. As further shown in FIG. 10, the process 1000 may include generating an ultrasound image corresponding to the scan plane of the ultrasound probe using the ultrasound data (operation 1020). For example, the processor 116 may generate an ultrasound image corresponding to the scan plane of the ultrasound probe 102. As further shown in FIG. 10, the process 1000 may including receiving tracking data from a tracking system (operation 1030). For example, the processor 116 may receive tracking data from the tracking system 200. As further shown in FIG. 10, the process 1000 may include determining a movement direction of the ultrasound probe relative to the ultrasound image using the tracking data. For example, the processor 116 may determine a movement direction of the ultrasound probe 102 relative to the ultrasound image using the tracking data.

Figure 11:
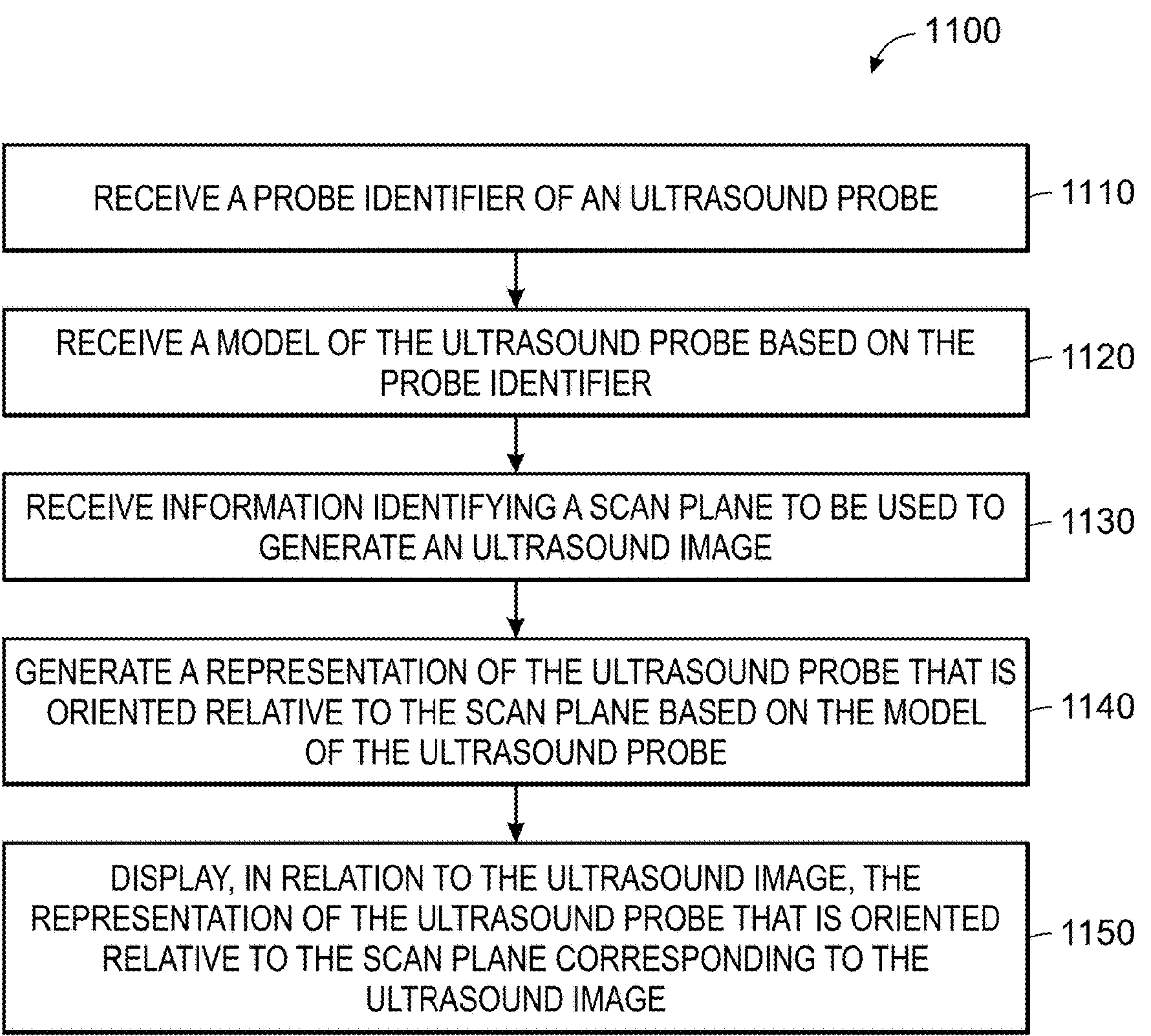
FIG. 11 is a flowchart of an example process for displaying a representation of an ultrasound probe based on a model of the ultrasound probe.

FIG. 11 is a flowchart of an example process 1100 for displaying a representation of an ultrasound probe 102 based on a model of the ultrasound probe 102. As shown in FIG. 11, the process 1110 may include receiving a probe identifier of an ultrasound probe (operation 1110). For example, the processor 116 may receive a probe identifier of the ultrasound probe 102 based on the ultrasound probe 102 being connected to the ultrasound system 100, based on a user input, based on preconfigured information, or the like. As further shown in FIG. 11, the process 1100 may include receiving a model of the ultrasound probe based on the probe identifier (operation 1120). For example, the processor 116 may receive a model of the ultrasound probe 102 by requesting the model from another device using the probe identifier, by identifying the model from stored information using the probe identifier, or the like. The model may be a 3D model, a 2D model, or the like, of the ultrasound probe 102. As further shown in FIG. 11, the process 1100 may include receiving information identifying a scan plane to be used to generate an ultrasound image (operation 1130). For example, the processor 116 may receive information identifying a scan plane to be used to generate an ultrasound image. As further shown in FIG. 11, the process 1100 may include generating a representation of the ultrasound probe that is oriented relative to the scan plane based on the model of the ultrasound probe 102 (operation 1140). For example, the processor 116 may generate a representation of the ultrasound probe 102 that is oriented relative to the scan plane based on the model of the ultrasound probe 102. As an example, the processor 116 may determine a side of the ultrasound probe 102 that is perpendicular to the scan plane, and generate the representation to display the side of the ultrasound probe 102. As further shown in FIG. 11, the process 1100 may include displaying, in relation to the ultrasound image, the representation of the ultrasound probe that is oriented relative to the scan plane corresponding to the ultrasound image (operation 1150). For example, the processor 116 may display, in relation to the ultrasound image, the representation of the ultrasound probe 102 that is oriented relative to the scan plane corresponding to the ultrasound image.

In light of the foregoing, some embodiments of the present disclosure provide an ultrasound system that determines a movement direction of an ultrasound probe relative to an ultrasound image, and displays a visual indicator that indicates the movement direction of the ultrasound probe relative to the ultrasound image. A viewer of the ultrasound image may quickly and efficiently ascertain the spatial relationship between the ultrasound probe and the ultrasound image. Further, the viewer may correctly, or more efficiently, manipulate the ultrasound probe to acquire ultrasound images of a region of interest. In this way, some embodiments of the present disclosure conserve resources of the ultrasound system, reduce the duration of the scanning, or the like, which might improve patient safety and outcomes during interventional procedures.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A method comprising:

receiving, from an ultrasound probe, first ultrasound data corresponding to a first scan plane of the ultrasound probe, second ultrasound data corresponding to a second scan plane of the ultrasound probe that is orthogonal to the first scan plane, and third ultrasound data corresponding to a third scan plane of the ultrasound probe that is orthogonal to the first scan plane and the second scan plane;

generating a first ultrasound image corresponding to the first scan plane of the ultrasound probe using the first ultrasound data, a second ultrasound image corresponding to the second scan plane of the ultrasound probe using the second ultrasound data, and a third ultrasound image corresponding to the third scan plane of the ultrasound probe using the third ultrasound data;

displaying the first ultrasound image corresponding to the first scan plane of the ultrasound probe, the second ultrasound image corresponding to the second scan plane of the ultrasound probe, and the third ultrasound image corresponding to the third scan plane of the ultrasound probe;

displaying a first representation of the ultrasound probe that is oriented relative to the first scan plane corresponding to the first ultrasound image, a second representation of the ultrasound probe that is oriented relative to the second scan plane corresponding to the second ultrasound image, and a third representation of the ultrasound probe that is oriented relative to the third scan plane corresponding to the third ultrasound image;

determining a first movement direction in which the ultrasound probe has moved relative to the first ultrasound image based on a movement of the ultrasound probe by an operator, a second movement direction in which the ultrasound probe has moved relative to the second ultrasound image based on the movement of the ultrasound probe by the operator, and a third movement direction in which the ultrasound probe has moved relative to the third ultrasound image based on the movement of the ultrasound probe by the operator; and displaying a first visual indicator in relation to the first representation of the ultrasound probe that indicates the movement direction in which the ultrasound probe has moved relative to the first ultrasound image based on the movement, a second visual indicator in relation to the second representation of the ultrasound probe that indicates the second movement direction in which the ultrasound probe has moved relative to the second ultrasound image based on the movement, and a third visual indicator in relation to the third representation of the ultrasound probe that indicates the movement direction in which the ultrasound probe has moved relative to the third ultrasound image based on the movement.

2. The method of claim 1, further comprising:

determining a first movement magnitude of the ultrasound probe in the first movement direction, a second movement magnitude of the ultrasound probe in the second movement direction, and a third movement magnitude of the ultrasound probe in the third movement direction; and generating the first visual indicator to reflect the first movement magnitude, the second visual indicator to reflect the second movement magnitude, and the third visual indicator to reflect the third movement magnitude.

3. The method of claim 1, wherein the determining the first movement direction, the second movement direction, and the third movement direction comprises determining the first movement direction, the second movement direction, and the third movement direction using a motion estimation technique.

4. The method of claim 1, wherein the determining the first movement direction, the second movement direction and the third movement direction comprises determining the first movement direction, the second movement direction, and the third movement direction using motion data received from the ultrasound probe.

5. The method of claim 1, wherein the determining the first movement direction, the second movement direction, and the third movement direction comprises determining the first movement direction, the second movement direction, and the third movement direction using tracking data received from a tracking system.

6. The method of claim 1, further comprising:

receiving a probe identifier of the ultrasound probe;

receiving a model of the ultrasound probe based on the probe identifier; and generating the first representation, the second representation, and the third representation of the ultrasound probe based on the model of the ultrasound probe.

7. The method of claim 1, wherein the determining the first movement direction, the second movement direction, and the third movement direction comprises determining the first movement direction, the second movement direction, and the third movement direction based on flow imaging data.

8. A device comprising:

a memory configured to store instructions; and one or more processors configured to execute the instructions to perform operations comprising:

receiving, from an ultrasound probe, first ultrasound data corresponding to a first scan plane of the ultrasound probe, second ultrasound data corresponding to a second scan plane of the ultrasound probe that is orthogonal to the first scan plane, and third ultrasound data corresponding to a third scan plane of the ultrasound probe that is orthogonal to the first scan plane and the second scan plane;

generating a first ultrasound image corresponding to the first scan plane of the ultrasound probe using the first ultrasound data, a second ultrasound image corresponding to the second scan plane of the ultrasound probe using the second ultrasound data, and a third ultrasound image corresponding to the third scan plane of the ultrasound probe using the third ultrasound data;

displaying the first ultrasound image corresponding to the first scan plane of the ultrasound probe, the second ultrasound image corresponding to the second scan plane of the ultrasound probe, and the third ultrasound image corresponding to the third scan plane of the ultrasound probe;

displaying a first representation of the ultrasound probe that is oriented relative to the first scan plane corresponding to the first ultrasound image, a second representation of the ultrasound probe that is oriented relative to the second scan plane corresponding to the second ultrasound image, and a third representation of the ultrasound probe that is oriented relative to the third scan plane corresponding to the third ultrasound image;

determining a first movement direction in which the ultrasound probe has moved relative to the first ultrasound image based on a movement of the ultrasound probe by an operator, a second movement direction in which the ultrasound probe has moved relative to the second ultrasound image based on the movement of the ultrasound probe by the operator, and a third movement direction in which the ultrasound probe has moved relative to the third ultrasound image based on the movement of the ultrasound probe by the operator; and displaying a first visual indicator in relation to the first representation of the ultrasound probe that indicates the movement direction in which the ultrasound probe has moved relative to the first ultrasound image based on the movement, a second visual indicator in relation to the second representation of the ultrasound probe that indicates the second movement direction in which the ultrasound probe has moved relative to the second ultrasound image based on the movement, and a third visual indicator in relation to the third representation of the ultrasound probe that indicates the movement direction in which the ultrasound probe has moved relative to the third ultrasound image based on the movement.

9. The device of claim 8, wherein the operations further comprise:

determining a first movement magnitude of the ultrasound probe in the first movement direction, a second movement magnitude of the ultrasound probe in the second movement direction, and a third movement magnitude of the ultrasound probe in the third movement direction; and generating the first visual indicator to reflect the first movement magnitude, the second visual indicator to reflect the second movement magnitude, and the third visual indicator to reflect the third movement magnitude.

10. The device of claim 8, wherein the determining the first movement direction, the second movement direction, and the third movement direction comprises determining the first movement direction, the second movement direction, and the third movement direction using a motion estimation technique.

11. The device of claim 8, wherein the determining the first movement direction, the second movement direction and the third movement direction comprises determining the first movement direction, the second movement direction, and the third movement direction using motion data received from the ultrasound probe.

12. The device of claim 8, wherein the determining the first movement direction, the second movement direction, and the third movement direction comprises determining the first movement direction, the second movement direction, and the third movement direction using tracking data received from a tracking system.

13. The device of claim 8, wherein the operations further comprise:

receiving a probe identifier of the ultrasound probe;

receiving a model of the ultrasound probe based on the probe identifier; and generating the first representation, the second representation, and the third representation of the ultrasound probe based on the model of the ultrasound probe.

14. A method comprising:

receiving, from an ultrasound probe, first ultrasound data corresponding to a first scan plane of the ultrasound probe, second ultrasound data corresponding to a second scan plane of the ultrasound probe that is orthogonal to the first scan plane, and third ultrasound data corresponding to a third scan plane of the ultrasound probe that is orthogonal to the first scan plane and the second scan plane;

generating a first ultrasound image corresponding to the first scan plane of the ultrasound probe using the first ultrasound data, a second ultrasound image corresponding to the second scan plane of the ultrasound probe using the second ultrasound data, and a third ultrasound image corresponding to the third scan plane of the ultrasound probe using the third ultrasound data;

displaying the first ultrasound image corresponding to the first scan plane of the ultrasound probe, the second ultrasound image corresponding to the second scan plane of the ultrasound probe, and the third ultrasound image corresponding to the third scan plane of the ultrasound probe;

displaying a first representation of the ultrasound probe that is oriented relative to the first scan plane corresponding to the first ultrasound image, a second representation of the ultrasound probe that is oriented relative to the second scan plane corresponding to the second ultrasound image, and a third representation of the ultrasound probe that is oriented relative to the third scan plane corresponding to the third ultrasound image;

determining a first movement direction in which the ultrasound probe has moved relative to the first ultrasound image based on a movement of the ultrasound probe by an operator, a second movement direction in which the ultrasound probe has moved relative to the second ultrasound image based on the movement of the ultrasound probe by the operator, and a third movement direction in which the ultrasound probe has moved relative to the third ultrasound image based on the movement of the ultrasound probe by the operator; and displaying a first visual indicator in relation to the first representation of the ultrasound probe that indicates the movement direction in which the ultrasound probe has moved relative to the first ultrasound image based on the movement, a second visual indicator in relation to the second representation of the ultrasound probe that indicates the second movement direction in which the ultrasound probe has moved relative to the second ultrasound image based on the movement, and a third visual indicator in relation to the third representation of the ultrasound probe that indicates the movement direction in which the ultrasound probe has moved relative to the third ultrasound image based on the movement.

15. The method of claim 14, further comprising:

determining a first movement magnitude of the ultrasound probe in the first movement direction, a second movement magnitude of the ultrasound probe in the second movement direction, and a third movement magnitude of the ultrasound probe in the third movement direction; and generating the first visual indicator to reflect the first movement magnitude, the second visual indicator to reflect the second movement magnitude, and the third visual indicator to reflect the third movement magnitude.

16. The method of claim 14, wherein the determining the first movement direction, the second movement direction, and the third movement direction comprises determining the first movement direction, the second movement direction, and the third movement direction using a motion estimation technique.

17. The method of claim 14, wherein the determining the first movement direction, the second movement direction and the third movement direction comprises determining the first movement direction, the second movement direction, and the third movement direction using motion data received from the ultrasound probe.

18. The method of claim 14, wherein the determining the first movement direction, the second movement direction, and the third movement direction comprises determining the first movement direction, the second movement direction, and the third movement direction using tracking data received from a tracking system.

* * * * *